United States Patent [19]

Stull et al.

[11] 4,272,480

[45] Jun. 9, 1981

[54] DEVICE FOR REDUCING THE SENSITIVITY OF AN ETHYLENE OXIDE LEAK DETECTOR

[75] Inventors: Bertram O. Stull; Russell Reed, Jr., both of Ridgecrest, Calif.

[73] Assignee: The United State of America as represented by the Secretary of the Navy, Washington, D.C.

[21] Appl. No.: 124,369

[22] Filed: Feb. 25, 1980

[51] Int. Cl.³ .................... G01N 21/01; G01N 31/22
[52] U.S. Cl. .................................. 422/58; 23/232 R; 55/274; 422/86
[58] Field of Search .................. 23/232 R, 230 L; 422/58, 83, 86, 87; 435/31; 55/74, 274

[56] References Cited

U.S. PATENT DOCUMENTS

| | | |
|---|---|---|
| 2,998,306 | 8/1961 | Huyck et al. ............... 435/31 X |
| 3,000,706 | 9/1961 | Royce ........................ 435/31 X |
| 3,112,999 | 12/1963 | Grosskopf .................. 422/58 X |
| 3,258,312 | 6/1966 | Olson ......................... 422/83 X |
| 3,737,349 | 6/1973 | Levenson ......................... 149/2 |
| 3,856,465 | 12/1974 | Lipscomb .................... 23/230 L |
| 3,992,154 | 11/1976 | Whitbourne et al. . |

OTHER PUBLICATIONS

*The Merck Index*–8th Edition, Merck & Co., Inc., Rahway, N.J. 1968, p. 320.

Primary Examiner—Arnold Turk

[57] ABSTRACT

A device for monitoring for the presence of ethylene oxide gas comprising an indicator which undergoes color change in the presence of ethylene oxide and a scrubber system to keep the device from being too sensitive. The scrubber system preferably employs activated charcoal coated with silicotungstic acid as the scrubber material.

5 Claims, 1 Drawing Figure

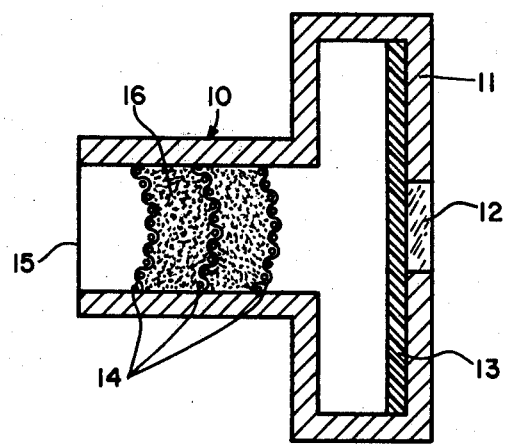

DEVICE FOR REDUCING THE SENSITIVITY OF AN ETHYLENE OXIDE LEAK DETECTOR

BACKGROUND OF THE INVENTION

1. Field of the Invention

This invention relates to a device for determining whether containers of ethylene oxide have developed leaks. More particularly, this invention relates to a device for detecting the presence of ethylene oxide gas.

2. Description of the Prior Art

Containers of volatile materials must often be packed in crates for shipping. One specific example is the packing for shipping of fuel air explosive warheads which commonly contain the volatile material, ethylene oxide.

While such containers are crated, it is desirable to be able to monitor them and determine whether or not they have developed leaks. This is done by monitoring for ethylene oxide gas.

In the past, various techniques have been used to monitor for ethylene oxide gas. Among these have been the use of infrared spectroscopy, microwave spectroscopy, hydrogen flame ionization, semiconductor gas-electric transduction, refracted index, electron capture, catalytic oxidation, Van der Waal's adsorption and chemical reaction with color change. Except for the last method, an energy source is required. Accordingly, the last method, which does not require an energy source, is preferred. However, the device presently utilized in carrying out the chemical reaction with color change technique has a serious drawback. That drawback is the fact that it is too sensitive.

The presently used device is so sensitive that it will detect ethylene oxide vapor present due to mere spillage on the surface of a container while the container was being filled. In addition, it is affected by heat, light, moisture and organic compounds other than ethylene oxide.

The presently used device employs, as the indicator, a small paper disc coated with approximately 0.018 grams of magnesium bromide hexahydrate and 0.003 grams of a combination of 1,8-dihydroxyanthroquinone (chrysazin) and polyvinyl acetate binder. The ethylene oxide reacts with the magnesium bromide hexahydrate to produce bromohydrin and magnesium hydroxide. The magnesium hydroxide, in turn, reacts with the chrysazin to cause a change in color from yellow to red.

Ethylene oxide will react with a number of other salts and water to produce similar products. This fact is sometimes used to make modifications of the aforementioned device for detecting ethylene oxide. Other materials that have been investigated include potassium thiocyanate, magnesium chloride and sodium thiosulfate. Devices utilizing these materials all have the sensitivity drawback of the presently used device.

BRIEF DESCRIPTION OF THE DRAWING

The single FIGURE of the drawing is a cross-sectional view of an ethylene oxide gas monitoring device according to this invention.

SUMMARY OF THE INVENTION

According to this invention, the sensitivity of an ethylene oxide detector device which employs a disc coated with materials which will interact to produce a color change upon exposure to ethylene oxide is reduced by means of a filter or scrubber system placed between the disc and the ethylene oxide vapor source.

The filter or scrubber system is made up of a scrubber material and means for holding it in place between the ethylene oxide source and the aforementioned disc. The holding means may be a series of screens or some other porous material such as paper. The preferred scrubber material is silicotungstic acid coated onto activated charcoal.

DESCRIPTION OF THE PREFERRED EMBODIMENTS

The purpose of an ethylene oxide gas monitoring device according to this invention is to detect the presence of relatively large amounts of ethylene oxide gas that will be present if an ethylene oxide canister which has been crated for shipping or merely stored has developed a leak. A leak may develop due to rough handling or a mishap and if it does it will be desirable to remove the canister from the presence of other similary crated or stored canisters and dispose of it.

The single FIGURE of the drawing depicts a cross-sectional view of an ethylene oxide gas monitoring device 10. The device is made up a housing 11, a window 12, an indicator 13, a plurality of screens 14 which hold scrubber material 16 in place or, in the alternative, are coated with scrubber material. The screens and their coating or the material they hold in place may be called a "scrubber system". The housing is preferably cylindrical but may have almost any geometrical shape.

The purposes of the housing are (1) to hold the indicator and scrubber system in place and (2) to provide an avenue through which ethylene oxide gas travels through the scrubber system to the indicator. This avenue is provided by leaving one end 15 of the device open. In order to get to the indicator, vapor must enter end 15 of the device and travel through the scrubber system.

The purpose of the window is to permit viewing of the indicator by an observer.

The purpose of the indicator is to provide one viewing the device with information regarding the presence or absence of a leak in an ethylene oxide canister (not shown). In use, the device is attached to or mounted in close proximity to an ethylene oxide canister that is to be monitored. The indicator carries out its purpose by changing color if ethylene oxide vapor is present. The indicator may employ magnesium bromide hexahydrate and chrysazine or any of the other materials set forth above.

The purpose of the scrubber system is to prevent the device from being overly sensitive. That is, it is not desirable to have the indicator change color merely because there is ethylene oxide gas present due to spillage on the surface of a canister while it was being filled or from some similar insignificant source. It is information regarding major sources and not minor sources that is sought from the device.

Reaction of ethylene oxide vapor with the silicotungstic acid in the scrubber prevents small amounts of the vapor from reaching the indicator. If sufficient ethylene oxide vapor is present to exceed the reactive capacity of the scrubber and affect the indicator, it is more reliably indicative of a leaking container.

To perform its function according to this invention, the scrubber system preferably employs activated charcoal coated with silicotungstic acid as the scrubber material. The silicotungstic acid is actually the scrubber material. The activated charcoal is utilized to (1) present a large surface area upon which the silicotungstic acid can react with ethylene oxide and to (2) absorb some of the reaction products that result when ethylene oxide and silicotungstic acid react. Tests have indicated that the incorporation of silicotungstic acid particles themselves (without the charcoal) into a monitoring device is impractical because the products of the reaction between ethylene oxide and silicotungstic acid are liquid.

Silicotungstic acid may be coated onto activated charcoal by dissolving the acid in water, adding charcoal to the solution and stirring the solution while passing air through it until the particles appear dry. Some of the water evaporates. Most is absorbed by the charcoal. The following Table sets forth suitable amounts of materials which may be used in the preparation of a 300 gram batch.

TABLE

Silicotungstic Acid—75.0 grams
Activated Charcoal (6–14 mesh)—225.0 grams
Water—60.0 grams Once prepared, the silicotungstic acid coated charcoal is inserted among the screens 14 depicted in the drawing so that the screens can hold the coated charcoal particles in place. The screens, of course, must be of such a mesh as to prevent the particles of silicotungstic acid coated particles from passing through. The drawing shows three screens. The number of screens is not critical. Any number of screens could be used. In fact, other holding devices such as porous paper could be used.

The presence of moisture due to the method of preparation of the silicotungstic acid coated activated charcoal may interfere with the effectiveness of the scrubber material. Moisture has no effect if the scrubber material is used at temperatures of on the order of 140° F. and undried material is marginally useful at 70° F. However, the scrubber material is not ordinarily used at 140° F. and is ordinarily used at temperatures of about 70° F. Therefore, it is preferable that moisture be removed. This may be done by drying the coated charcoal particles at about 100° C. for about 20 hours.

Experiments have shown that from about 2 to 10 grams of scrubber material in a scrubber device having a tubular shaped avenue about 1 to 1.5″ in diameter and about 1 to 2″ long through which ethylene oxide vapor must pass to get to the indicator will eliminate the aforementioned oversensitivity problem. It readily follows from this discussion that densely packed scrubber material will be more effective in keeping out ethylene oxide vapor than will extremely loosely packed material. On the other hand a device containing densely packed material will be significantly less sensitive than a device containing loosely packed material. How much scrubber material one puts into a scrubber system will be dictated by the amount of sensitivity desired.

The drawing depicts a cylindrical housing with a large end designed to hold the indicator and a smaller end adapted to permit vapors to flow through it toward the indicator. It will be apparent to those skilled in the art that the housing could be of almost any shape or could even be disposed of. All that is required to carry out the purposes of this invention is a means for forcing vapors to pass through the scrubber material before they reach the indicator.

The device shown in the drawing is convenient for use because its metallic housing may be supported in the general area of a potential source of ethylene oxide by many types of brackets. Almost any metal can be used to form the housing. Steel is convenient to use.

To use the device, one may hang it or simply lay it near a potential source of vapor and observe the indicator at regular intervals. The window used in the device may be glass or any other material that will permit viewing and not react adversely with the indicator adjacent to it.

What is claimed is:

1. A device for determining the presence of ethylene oxide vapor, said device comprising:
   A. an indicator which indicates the presence of ethylene oxide vapor if it comes into contact with ethylene oxide vapor;
   B. a housing for supporting said indicator in an area of potential vapor source;
   C. a scrubber system in said housing;
   D. said scrubber system being supported adjacent to said indicator between said indicator and said potential vapor source; and
   E. said scrubber system comprising activated charcoal coated with silicotungstic acid and being effective to block a certain amount of ethylene oxide vapor from reaching said indicator.

2. A device according to claim 1 wherein said scrubber system further comprises a plurality of screens to hold the activated charcoal coated with silicotungstic acid in place in said housing.

3. A device according to claim 2 wherein said housing is substantially tubular in shape with an open end and a closed end, wherein said closed end is equipped with a window, wherein said indicator is mounted in said tube adjacent to said window and wherein said scrubber system is mounted within said tube between said indicator and said open end.

4. A device according to claim 1 wherein said scrubber system further comprises a plurality of sheets of porous paper to hold the activated charcoal coated with silicotungstic acid in place in said housing.

5. A device according to claim 6 wherein said housing is substantially tubular in shape with an open end and a closed end, wherein said closed end is equipped with a window, wherein said indicator is mounted in said tube adjacent to said window and wherein said scrubber system is mounted within said tube between said indicator and said open end.

* * * * *